United States Patent [19]

Nakashima et al.

[11] 4,335,102
[45] * Jun. 15, 1982

[54] ORAL COMPOSITION FOR CARIES PROPHYLAXIS

[75] Inventors: Syozi Nakashima, Hatano; Tosiyuki Ozawa, Minami-ashigara; Takeshi Naganuma, Odawara; Takashi Ujiie, Ninomiya; Satoshi Hayashi, Hiratsuka; Yoshihito Ochiai, Fujisawa, all of Japan

[73] Assignee: Lion Corporation, Tokyo, Japan

[*] Notice: The portion of the term of this patent subsequent to Mar. 31, 1998, has been disclaimed.

[21] Appl. No.: 185,964

[22] Filed: Sep. 9, 1980

[30] Foreign Application Priority Data

Sep. 20, 1979 [JP] Japan ............................... 54-121194

[51] Int. Cl.$^3$ ........................... A61K 7/18; A61K 9/68
[52] U.S. Cl. ......................................... 424/52; 424/48
[58] Field of Search .......................................... 424/52

[56] References Cited

U.S. PATENT DOCUMENTS

| | | | |
|---|---|---|---|
| 2,946,725 | 7/1960 | Norris et al. | 424/52 |
| 3,105,798 | 10/1963 | Holliday et al. | 424/52 |
| 3,282,792 | 11/1966 | Fiscella | 424/52 |
| 3,544,678 | 12/1970 | Griebstein | 424/52 |
| 3,549,677 | 12/1970 | Griebstein et al. | 424/49 X |
| 3,934,002 | 1/1977 | Haefele | 424/54 |
| 4,259,316 | 3/1981 | Nakashima et al. | 424/52 |

FOREIGN PATENT DOCUMENTS

| | | |
|---|---|---|
| 804486 | 11/1958 | United Kingdom . |
| 845611 | 8/1964 | United Kingdom . |
| 1160640 | 8/1969 | United Kingdom . |
| 1222197 | 2/1971 | United Kingdom . |
| 1384375 | 2/1975 | United Kingdom . |
| 1408922 | 10/1975 | United Kingdom . |

OTHER PUBLICATIONS

Muhler et al., J.A.D.A. 51, 665 (1955).

Primary Examiner—Frank Cacciapaglia, Jr.
Attorney, Agent, or Firm—Birch, Stewart, Kolasch & Birch

[57] ABSTRACT

An oral composition for caries prophylaxis which comprises a highly soluble stannous compound such as stannous fluoride preferably in an amount of 0.03 to 5% by weight of the composition as stannous tin, a difficultly soluble stannous compound such as stannous pyrophosphate preferably in an amount of 0.05 to 10% by weight of the composition as stannous tin, a phytic acid compound such as sodium phytate preferably in an amount of 0.1 to 20% by weight of the composition, and the pH of the composition being preferably acidic. A portion of the difficultly soluble stannous compound may be in a precipitate form. The oral composition which may be used as dentifrices, prophylactic pastes, dental flosses and the like permits $n^{2+}$ ions to exert its effect because the storage stability is high enough to maintain the increased concentration of active dissolved stannous ions in the composition for a prolonged period of time and can render the tooth enamel more resistant to acid attack when applied to teeth.

16 Claims, No Drawings

ORAL COMPOSITION FOR CARIES PROPHYLAXIS

BACKGROUND OF THE INVENTION

This invention relates to oral compositions for use as dentifrices, topical solutions or pastes, desensitizers, prophylactic pastes, mouthwashes, disintegratable tablets, oral bands, cavity sealers, gels for ultrasonic treatment, gels for iontophoresis, dental flosses, chewing gum and the like. More particularly, this invention relates to oral compositions which contain a relatively highly soluble stannous compound such as stannous fluoride, a relatively difficultly soluble stannous compound such as stannous pyrophosphate, a phytic acid compound, and optionally, a fluorine compound and which are effective for the prophylaxis of dental caries and paradental diseases as exemplified by increased acid resistance of the tooth enamel treated therewith. It is well known that stannous compounds, when applied in the form of a solution or the like, can provide tooth enamel and dentin with an improved acid resistance due to the action of stannous ions. It is also known that when teeth are treated with those solutions additionally containing fluorine ions, for example, those containing stannous fluoride $SnF_2$ or stannous chloride fluoride $SnClF$, not only the acid resistance of the tooth enamel is improved by stannous ions, but fluorine is also taken up by the tooth enamel, with outstanding results of caries inhibition, caries control, desensitization of hypersensitive dentin. (See J. C. Muhler et al, J.A.D.A., 51, 665 (1955)).

For the above reason, it was a common practice to apply stannous compound solutions to teeth or to blend stannous compounds into oral compositions such as dentifrices. Unfortunately, stannous compound solutions are not stable during storage and active dissolved stannous ions are likely to deactivate. Aqueous solutions of stannous fluoride are most widely used, but readily show a reduced efficacy in caries prophylaxis because as a result of hydrolysis or atmospheric oxidation, stannous ions contained therein tend to be converted into inert tin compounds (insoluble tin hydroxide, tin oxide, tin oxyfluoride, stannic tin compounds, etc.) which cannot produce the above-mentioned effect, and consequently the quantity of active dissolved stannous ions is considerably reduced. The lower the concentration of stannous fluoride is and the higher the storage temperature is, the more outstanding this tendency is. In the case of dentifrices containing stannous fluoride, stannous fluoride tends to react with other ingredients to form insoluble tin hydroxide, tin phosphate and the like, and soluble but highly stable complexes, resulting in a reduced quantity of active free stannous ions. This tendency is outstanding at pH 6.0 or higher. Furthermore, hydrolysis or dissolved oxygen causes $Sn^{2+}$ in dentifrices to be oxidized into $Sn^{4+}$. This causes a further reduction of the quantity of active dissolved stannous ions. Accordingly, the effect of blending stannous fluoride into dentifrices is not fully attained.

To prevent reduction of the quantity of active dissolved stannous ions during storage, a variety of attempts have been made. For instance, U.S. Pat. No. 2,946,725 and British Pat. Nos. 804,486 and 845,611 disclose a dentifrice containing a stannous compound, said stannous compound being difficultly soluble but capable of dissolving to supply at least 10 but not more than 1000 parts per million of stannous ions when in association with water, and being present in said dentifrice in an amount sufficient to provide said stannous compound in undissolved and undissociated form. These difficultly soluble stannous compounds such as stannous pyrophosphate, stannous metaphosphate and stannous tartrate are blended as a "reservoir" into dentifrices together with soluble stannous compounds such as stannous fluoride. The difficultly soluble stannous compound serves to supply a small quantity of stannous ions for a prolonged period of time to maintain the concentration of stannous ions constant. Another approach is to stabilize stannous ion by adding a certain type of organic chelating or complexing agents. Examples of such agents are carboxylic acids such as malic acid, citric acid and their salts as disclosed in U.S. Pat. No. 3,282,792; hydroxyethyl nitrilodiacetic acid and its salts as disclosed in U.S. Pat. No. 3,544,678; aldonic acid and its derivatives as disclosed in U.S. Pat. No. 3,105,798; and methane diphosphonic acid, ethane-1-hydroxy-1,1-diphosphonic acid and their derivatives as disclosed in U.S. Pat. No. 3,549,677 and British Pat. No. 1,160,640.

However, when difficultly soluble stannous compounds are blended as a "reservoir" particularly into relatively viscous systems such as dentifrices, gels and prophylaxis pastes, such compounds cannot always have a sufficient capability of supplying dissolved stannous ions, resulting in a considerable reduction of active dissolved stannous ions with time. Furthermore, the acid resistance of tooth enamel is not fully improved as shown in Experiments described below.

Stannous compounds, particularly fluorine ion-containing stannous compounds such as stannous fluoride produce an effect of improving the acid resistance of the tooth enamel to some extent. However, such stannous compounds are not fully effective when used alone.

Other investigations have been made on a variety of compounds having caries inhibitory effect. For example, an attempt was made to use sodium and potassium phytates to reduce the the solubility of hydroxyapatite in acid. However, the effect of these phytates has not been generally recognized. Other examples using phytic acid are British Pat. No. 1,384,375 which discloses an oral hygiene composition comprising a divalent metal salt of phytic acid such as calcium phytate mixed with a monofluorophosphate, and British Patent No. 1,408,922 which discloses an oral composition comprising two separate phases, one phase containing a water-soluble calcium compound and the other phase containing a water-soluble organic or inorganic phosphoric acid compound such as phytic acid and optionally, a water-soluble fluorine compound. However, the evaluation of these compositions has not been widely established. U.S. Pat. No. 3,934,002 also discloses toothpastes containing sodium phytate. British Pat. No. 1,222,197 discloses the use of inorganic or organic phosphorus compounds.

SUMMARY OF THE INVENTION

An object of this invention is to provide an oral composition which can render the tooth enamel more resistant to acid attack without the decrease of the effectiveness for a prolonged period of time because the efficacy is scarcely reduced by the self-cleaning action of saliva, brushing, mastication and the like.

Another object of this invention is to provide an oral composition which permits stannous ion to exert its effect both over a wide pH range and after a long term storage because the storage stability is high enough to maintain the increased concentration of active dissolved stannous ions in the composition for a prolonged period of time.

As a result of a study on oral compositions containing stannous compounds in order to eliminate an essential reduction of the efficacy of the compositions with time and to permit stannous ion to exert its effect efficiently as well as improving the acid resistance of the tooth enamel, the inventors have found that the abovementioned objects can be attained by incorporating a phytic acid compound such as sodium phytate into an oral composition containing a relatively highly soluble stannous compound such as stannous fluoride and a relatively difficultly soluble stannous compound such as stannous pyrophosphate.

The quantities of stannous ions in a stannous system essentially consisting of a highly soluble stannous compound and a difficultly soluble stannous compound were measured before and after a long term storage in an oxidizing atmosphere to find that these quantities of dissolved stannous ions were both very low. This stannous system was found to be not so highly effective to improve the acid resistance of tooth enamel treated therewith. An attempt to add a variety of chelating and complexing agents to stannous systems containing both highly and difficultly soluble stannous compounds failed to produce increased powers of solubilizing and stabilizing stannous ions and increased effect of improving the acid resistance of tooth enamel. A slight increase of the solubilizing power was observed only when citric acid, oxalic acid, EDTA or tannic acid was added. However, these acids were insufficient to improve the acid resistance of tooth enamel or to supply and maintain active dissolved stannous ions.

Making a further research, the inventors have found that addition of a phytic acid compound to a stannous system containing both highly and difficultly soluble stannous compounds can minimize or eliminate the reduction of the quantity of active dissolved stannous ions even after aging of the system for a long term in an oxidizing atmosphere, and that the acid resistance of the tooth enamel treated with the phytic acid containing composition is remarkably improved over when treated with aqueous stannous fluoride solutions. The effect due to the addition of a phytic acid compound is fully exerted over a wide pH range of 2 to 7 even in dentifrices. Particularly when a phytic acid compound is added to a system containing a highly soluble stannous compound and a difficultly soluble stannous compound which is partially in undissociated form as a precipitate, the phytic acid compound promotes the dissociation of the difficultly soluble stannous compound (reservoir) in the form of a precipitate, that is, ensures constant supply of stannous ions by permitting the difficultly soluble stannous compound to become gradually soluble at a proper level for a prolonged period of time, and increases the storage stability of stannous ion without adversely affecting the reactivity of stannous ion, but rather enhancing the effectiveness of stannous ion. In summary, the phytic acid compound not only ensures constant supply of active dissolved stannous ions and improved maintenance of the activity of stannous ion, but also coacts with stannous ion synergistically to further improve the acid resistance of tooth enamel over when stannous systems are applied without the addition of the phytic acid compound.

According to this invention, there is provided an oral composition for caries prophylaxis comprising:
a highly soluble stannous compound preferably in an amount of 0.03 to 5% by weight of the composition as stannous tin,
a difficultly soluble stannous compound preferably in an amount of 0.05 to 10% by weight of the composition as stannous tin, and
a phytic acid compound preferably in an amount of 0.1 to 20% by weight of the composition.

Since a phytic acid compound is incorporated into a system containing both highly and difficultly soluble stannous compounds, the oral composition according to this invention has advantages that stannous ion can exert its effect over a wide pH range of 2 to 7 and be more reactive with the tooth enamal such that the tooth enamel (enamel surface) treated with the composition is made more resistant against acid attack.

When a portion of the difficultly soluble stannous compound is present as a precipitate or in an undissociated form, the concentration of active dissolved stannous ions in the oral composition is maintained in a stable manner during an extended storage period. The effect of stannous ion is fully produced after such long term aging. The use of the phytic acid compound in combination with the partially precipitated difficultly soluble stannous compound ensures the storage stability and high reactivity with the tooth enamel of stannous ion in the pH range of 2 to 7 usually employed for dentifrices, without causing any problem in the preparation of dentifrices, gels or prophylaxis pastes.

When the oral composition according to this invention additionally containing fluorine ion is applied to teeth, fluorine is taken up by the tooth enamel at a high retentivity such that the fluorine is not readily washed away. This is very advantageous for dental caries prophylaxis.

The above and other objects, features and advantages of this invention will be more clearly understood from the following detailed description, examples and claims.

DETAILED DESCRIPTION OF THE INVENTION

The highly soluble stannous compounds which can be used in the oral composition of this invention include stannous fluoride, stannous chloride, stannous chloride fluoride, stannous acetate, sodium stannous fluoride, potassium stannous fluoride, stannous hexafluorozirconate, stannous sulfate, stannous tartrate, stannous gluconate, etc. and mixtures thereof. These highly soluble stannous compounds form a predominant source of dissolved stannous ions in the oral composition. The amount of the highly soluble stannous compound is not necessarily limited, but may preferably be at least 0.03% by weight of the oral composition, more preferably at least 0.1% by weight of the oral composition as stannous tin in order to obtain a satisfactory effect of dissolved stannous ion. The upper limit of the amount of the highly soluble stannous compound may preferably be 5%, more preferably 3% by weight as stannous tin. The highly soluble stannous compound may be used in excess of its saturation level such that the excessive portion precipitates. For stannous fluoride, the optimum blending amount ranges from 0.08 to 3% by weight of the composition.

The difficultly soluble stannous compounds which can be used in the oral composition according to this invention include stannous pyrophosphate, stannous metaphosphate, stannous oxide, stannous oxalate, stannous phosphate, etc. and mixtures thereof. The amount of the difficultly soluble stannous compound varies with the amounts of the highly soluble stannous compound and the phytic acid compound and is generally in the range of 0.05 to 10%, more preferably 0.05 to 5% by weight of the composition as stannous tin. The preferred blending range is 0.1 to 3% for stannous pyrophosphate, 0.1 to 2% for stannous metaphosphate, and 0.1 to 2% for stannous oxalate. The difficultly soluble stannous compound is preferably blended in amounts such that a portion of the compound is a precipitate or in an undissociated form. The precipitate of this difficultly soluble stannous compound acts as a "reservoir" of stannous ions, enabling to maintain the quantity of active dissolved stannous ions at a substantially constant level for a prolonged period of time.

The phytic acid compounds which can be used in the present invention include phytic acid and metal salts of phytic acid in which all or some of the hydrogen atoms in the phosphate groups at the 1- to 6-positions of phytic acid are replaced by metal substituents, for example, alkali metal salts of phytic acid such as sodium phytate, potassium phytate and lithium phytate, ammonium phytate, divalent metal salts of phytic acid such as magnesium phytate, zinc phytate and calcium phytate, aluminum phytate and phytin, and double salts thereof. Mixtures of any of these salts are also included. Particularly preferred are those soluble in water. More preferably, the phytic acid compound is selected from the group consisting of phytic acid, sodium phytate, potassium phytate, lithium phytate, ammonium phytate and mixtures thereof.

In the present invention, myo-inocitolpentaphosphoric acid especially having a hydroxy group at the 2-position and metal salts thereof fall under the category of the phytic acid compound of the present invention.

By blending the phytic acid compound, elution of stannous ions from the difficulty soluble stannous compound is promoted, the storage stability of stannous ions is increased, and stannous ions are maintained active. Blending of the phytic acid compound permits stannous ion to exert its effect and as a result of the synergistic effect with stannous ion, contributes to improving the acid resistance of tooth enamel. The amount of the phytic acid compound is not particularly limited, but may preferably be 0.1 to 20%, more preferably 0.4 to 15%, especially 0.5 to 3% by weight of the composition.

In the oral composition according to this invention, a fluorine compound may be used in addition to the essential ingredients, highly and difficultly soluble stannous compounds and phytic acid compound. The coexistence of fluorine ion is very effective for caries prophylaxis. The fluorine compounds which can be used include sodium fluoride, potassium fluoride, lithium fluoride, ammonium fluoride, sodium monofluorophosphate, sodium hydrogen monofluorophosphate, potassium monofluorophosphate, ammonium monofluorophosphate, potassium hexafluorozirconate, potassium hexafluorotitanate, and mixtures thereof. Also included are cesium fluoride, nickel fluoride, zirconium fluoride, silver fluoride, hexylamine hydrofloride, laurylamine hydrofluoride, cetylamine hydrofluoride, glycine hydrofluoride, lysine hydrofluoride, alanine hydrofluoride and the like.

The fluorine compound is blended in the oral composition so as to give a total concentration of fluorine of preferably 50-10,000 parts per million, more preferably 200-10,000 ppm. In preparing dentifrices, the total amount of fluorine may preferably be not more than 1000 ppm.

The oral composition according to this invention may further include additional well-known ingredients depending on the type and form of a particular oral composition. Any desired known ingredients may be mixed with the highly and difficultly soluble stannous compounds, the phytic acid compound and optionally the fluorine compound in water to produce an oral composition. The application forms of the oral composition according to this invention include dentifrices, topical solutions or pastes, disintegratable tablets, oral bands, cavity sealers, gels for ultrasonic treatment, gels for iontophoresis, prophylactic pastes, dental flosses, desensitizers of teeth, mouthwashes in the form of liquids, tablets, powders and gels, chewing gum and the like.

Liquid mouthwashes and topical solutions, for example, may be prepared by adding highly and difficultly soluble stannous compounds, a phytic acid compound and optionally a fluorine compound to a suitable solvent such as distilled or deionized water and ethanol. Sweetening agents such as saccharine, etc., and flavoring agents such as peppermint oil, spearmint oil, anise oil, etc. may also be added in small amounts, if desired. Gel-type mouthwashes and topical pastes may be prepared by adding to the above-prepared solution a humectant such as glycerin, sorbitol, propylene glycol, polyethylene glycol and the like in an amount of 5-70 wt%, a binder such as xanthan gum, guar gum, carrageenan, hydroxyethyl cellulose, sodium carboxymethyl cellulose and the like in an amount of 0.3-10 wt%, and an antiseptic agent such as ethyl parahydroxybenzoate, butyl parahydroxybenzoate and the like in a minor amount. Further, tablets and powders may be prepared in a usual manner using well-known tablet or powder-forming agents, for example, a vehicle such as lactose and mannitol, a disintegrator and a binder such as corn starch and carboxymethyl cellulose, etc.

Oral bands may be prepared by dissolving or dispersing in water stannous compounds, a phytic acid compound and optionally a fluorine compound together with necessary components, for example, a tacky high-molecular substance soluble in water or changing into a gel in water such as sodium carboxymethyl cellulose, methyl cellulose, hydroxyethyl cellulose, hydroxypropyl cellulose, polyvinyl alcohol, polyvinylpyrrolidone, sodium polyacrylate, sodium alginate, dextran, gelatin, carrageenan and the like in a usual blending amount of 20-99 wt%; a polyhydric alcohol such as polyethylene glycol, propylene glycol, sorbitol, glycerin and the like in a usual blending amount of 1-50 wt%; and a surface-active agent such as an anion active agent and a nonion active agent (e.g. polyoxyethylene stealate or polyoxyethylene sorbitan monooleate) in a usual blending amount of 0-30 wt%. The resulting solution or dispersion is freeze dried to remove water and form a film which is cut into a desired shape.

Dentifrices may include an abrasive such as calcium pyrophosphate, insoluble alkali metal metaphosphates (e.g. insoluble sodium metaphosphate), titanium dioxide, resins, aluminium oxide, aluminum hydroxide, silica (hydrated or anhydrated), aluminosilicate, zirconium silicate, magnesium silicate and the like in a usual blending amount of 20-60 wt%. Among them, insoluble alkali metal metaphosphates and silica are preferred. Dentifrices may also include a binder such as xanthan gum, guar gum, carrageenan, hydroxyethyl cellulose, propylene glycol alginate, sodium carboxymethyl cellulose, sodium carboxylmethyl hydroxyethyl cellulose, gum karaya, gum arabic, gum tragacanth, colloidal magnesium aluminum silicate, finely divided silica, Irish Moss, sodium alginate and the like in a usual blending amount of 0.5-5 wt%; a humectant such as glycerin, sorbitol and other polyhydric alcohols in a usual blending amount of 15-40 wt%; a foaming agent such as water-soluble salts of the higher alkyl sulfates having 8 to 18 carbon atoms in the alkyl group (e.g. sodium lauryl sulfate), water-soluble salts of alkylbenzene sulfonate (e.g. sodium dodecylbenzene sulfonate), water-soluble salts of sulfonated monoglycerides of higher fatty acids having 10 to 18 carbon atoms in the fatty acid group (e.g. sodium coconut monoglyceride sulfonate), higher fatty acid sodium monoglyceride monosulfates, salts of amides of higher fatty acid having 12 to 16 carbon atoms in the fatty acid group with lower aliphatic amino acids (e.g. sodium-N-methyl-N-palmitoyl tauride, sodium N-lauroyl sarcosinate, or sodium N-lauroyl L-glutamate), water-soluble salts of olefin sulfonates, sucrose fatty acid ester having 12 to 18 carbon atoms in the fatty acid group (e.g. sucrose monolaurate), alkyrol diethanol amide (e.g. lauroyl diethanol amide), condensates of sorbitan monostearate with approximately 60 moles of ethylene oxide, condensates of ethylene oxide with propylene oxide condensates of propylene glycol and the like in a usual blending amount of 0.5-3 wt%; a sweetening agent; a flavoring agent; an antiseptic agent; an anticariogenic agent such as chlorohexidine; and any other ingredients.

The oral composition of this invention is acidic. The pH of the composition may fall within the range of 2-7, more preferably 3-6 in order to derive the best results from the composition. The acidity may be adjusted to a desired level by adding an organic acid such as citric acid, tartaric acid, lactic acid, malonic acid, malic acid, L-ascorbic acid, acetic acid, succinic acid and gluconic acid or alkali metal salts thereof, an inorganic acid such as hydrochloric acid and phosphoric acid, or an alkali such as sodium hydroxide. The acidity may also be adjusted to phytic acid or its salt.

The oral composition of this invention may be used in an ordinary manner depending upon its type and form. For example, mouthwashes in the form of liquids may be applied with or without dilution with water while those in the form of tablets, powders or gels may be applied after they are dissolved or dispersed in water. Oral bands may be attached to teeth. Then the high-molecular substance which is the main component of the band is gelated and becomes tacky upon contact with saliva. With the tacky band firmly adhered to the teeth, the active ingredients (fluoride ions and the phytic acid compound) in the band act on the teeth. A topical solution or gel may be directly applied to a tooth surface.

As described above, the oral composition of this invention is applied to teeth directly or after it is prepared into a form suitable for oral application by diluting with, dissolving in or dispersing in water. Upon application to a tooth surface, stannous compounds and the phytic acid compound exhibit a synergistic effect on the tooth enamel, thereby substantially enhancing the acid resistance of the tooth enamel. The oral composition of this invention can be applied at room temperature or approximately 30° C. without a reduction in the acid resistance improvement. Further, the efficacy after application is retained for an extended period of time because the efficacy scarcely disappears out by the selfcleansing action of saliva, brushing, mastication and the like. It was found that the acid resistance of the tooth enamel treated with the present composition remains high even after the tooth is washed with running tap water for 24 hours. It was also found that stannous ions are stable in the composition for a long period of storage. This means that the present composition is an effective dental caries inhibitor which can be stored for an extended period of time and shows a prolonged activity after application.

The following examples are further illustrative of the present invention, but it is to be understood that the invention is not limited thereto. All percents in the examples are percents by weight unless otherwise specified. It should be noted that the pH of a composition is adjusted to a desired level by adding hydrochloric acid or sodium hydroxide.

EXAMPLE 1

A number of test solutions having the following composition were prepared using the chelating and complexing agents listed in Table 1. The pH of these solutions was adjusted to 5.0 by adding sodium hydroxide or hydrochloric acid.

| | |
|---|---|
| Stannous fluoride | 0.4% |
| Stannous pyrophosphate | 1.0% |
| Chelating or complexing agent | as shown in Table 1 |
| Water | balance |
| | 100.0% |

For each test solution, both immediately after preparation and after the solution had been stored for 10 days at 20° C. in an oxygen desiccator at 1 atmospheric pressure, the quantity of dissolved stannous ions and the Vickers hardness of an enamel block treated with the test solution and followed by acid decalcification were measured by the following methods. The results are shown in Table 1.

Measurement of the quantity of stannous ions

Quantitative analysis of stannous ions was conducted by the iodometric titration on a supernatant liquid obtained by removing a precipitate from each solution in a centrifugal separator (10,000-12,000 r.p.m.). The quantity of stannous ions dissolved in the supernatant liquid was determined using a 0.05 N iodine solution.

Measurement of Vickers hardness

An enamel block made of bovine enamel was immersed for 3 minutes in each of the test solutions at 30° C. Each block was brushed twenty times, that is, ten times in each of the longitudinal and transverse directions with a toothbrush, and then rinsed with water at 20° C. for 10-20 minutes. After rinsing, the enamel block was subjected to decalcification in an acidic solution (buffered solution of 0.1 M acetic acid, pH 4.5) at 20° C. for 2 hours. After decalcification, the hardness of the enamel block at the surface was measured with a Vickers hardness tester. The thus obtained Vickers hardness number (VHN) was used to evaluate the effect of the test solution on the acid resistance of the enamel.

TABLE 1

| Chelating and complexing agents | Amount* (%) | Initial Sn$^{2+}$ (%) | Initial VHN | After 10 days storage Sn$^{2+}$ (%) | After 10 days storage VHN | |
|---|---|---|---|---|---|---|
| Pentasodium phytate | 1.0 | 0.49 | 228 | 0.33 | 160 | The invention |
| Sodium citrate | 0.38 | 0.45 | 150 | 0.21 | 103 | Comparative |
| Malonic acid | 0.13 | 0.25 | 120 | 0.15 | 96 | " |
| L-ascorbic acid | 0.25 | — | 130 | — | 110 | " |
| Oxalic acid | 0.16 | 0.39 | 143 | 0.23 | 96 | " |
| Lactic acid | 0.12 | 0.28 | 120 | 0.18 | 80 | " |
| Tartaric acid | 0.20 | 0.32 | 148 | 0.13 | 86 | " |
| Benzoic acid | 0.16 | 0.31 | 133 | 0.18 | 93 | " |
| L-glutamic acid | 0.19 | 0.24 | 122 | 0.12 | 84 | " |
| Malic acid | 0.17 | 0.27 | 108 | 0.14 | 92 | " |
| Maleic acid | 0.15 | 0.22 | 120 | 0.12 | 81 | " |
| Fumaric acid | 0.15 | 0.21 | 110 | 0.12 | 85 | " |
| Adipic acid | 0.19 | 0.25 | 130 | 0.17 | 96 | " |
| Glutaric acid | 0.17 | 0.23 | 103 | 0.14 | 93 | " |
| L-aspartic acid | 0.17 | 0.23 | 105 | 0.13 | 89 | " |
| Succinic acid | 0.08 | 0.22 | 120 | 0.15 | 99 | " |
| Cinnamic acid | 0.19 | 0.21 | 118 | 0.10 | 75 | " |
| EDTA | 0.48 | 0.49 | 135 | 0.30 | 81 | Comparative |
| Tannic acid | 0.44 | 0.33 | 125 | 0.24 | 96 | " |
| None | — | 0.20 | 103 | 0.14 | 93 | " |

*Each of the chelating and complexing agents was blended in equal molar amount to 1.0% pentasodium phytate.

The results in Table 1 show that the use of a phytate not only contributes to the solubilization of tin in the initial solution, but also permits the quantity of stannous ions to be maintained at a sufficiently high level after a long term storage in an oxidizing atmosphere, improving the storage stability of the solution. The phytate is highly effective to retain the activity of stannous ion and to improve the acid resistance of the enamel.

For comparison, enamel blocks of bovine enamel were treated with an aqueous solution containing 1.0% pentasodium phytate at pH 2.8 and another aqueous solution containing 1.0% stannous fluoride at pH 2.8. Following the procedure described above, the blocks were subjected to decalcification and then the Vickers hardness was measured. Measurement was impossible for the former solution and a Vickers hardness number of 108 was obtained for the latter solution. These results indicate that acid resistance enhancement is outstanding when teeth are treated with a stannous fluoride/stannous pyrophosphate/phytate system.

The procedure of Example 1 was repeated except that pentasodium phytate was replaced by phytic acid and pentapotassium phytate. Similar results were obtained.

EXAMPLE 2

| | |
|---|---|
| Stannous fluoride | 0.4% |
| Stannous pyrophosphate | as shown in Tables 2–4 |
| Pentasodium phytate | as shown in Tables 2–4 |
| Water | balance |
| | 100.0% |

A number of test solutions having the above composition were prepared (the pH of the solutions was adjusted with sodium hydroxide or hydrochloric acid to 4.0–6.0). As described in Example 1, for each test solution, the quantity of dissolved stannous ions and the degree of improvement of enamel acid resistance (represented by the Vickers hardness number after decalcification of an enamel block treated with each test solution) were measured both immediately after preparation and after the solution had been stored for 7 days at 20° C. in an oxygen desiccator at 1 atmospheric pressure. The results are shown in Tables 2, 3 and 4.

TABLE 2

Vickers hardness after enamel decalcification (solution pH 5.0)

| | | Pentasodium phytate | | | | | | |
|---|---|---|---|---|---|---|---|---|
| | | 0% | | 1.0% | | 2.0% | | 3.0% |
| | | Initial | 7 days | Initial | 7 days | Initial | 7 days | Initial |
| Stannous pyrophosphate | 0% | 108 | 63 | 209* | 139* | 203* | 88* | 142* |
| | 0.5% | 102 | 72 | 230 | 155 | 183* | 107* | 174* |
| | 1.0% | 98 | 70 | 228 | 162 | 234 | 138 | 198* |
| | 2.0% | 113 | 72 | 209 | 170 | 218 | 160 | 178* |

TABLE 3

Quantity of dissolved Sn$^{2+}$ (percent) (solution pH 5.0)

| | | Pentasodium phytate | | | | | | |
|---|---|---|---|---|---|---|---|---|
| | | 0% | | 0.5% | | 1.0% | | 2.0% |
| | | Initial | 7 days | Initial | 7 days | Initial | 7 days | Initial | 7 days |
| Stannous pyrophosphate | 0% | 0.15 | 0.10 | 0.24 | 0.15 | 0.29* | 0.09* | 0.30* | 0.03* |
| | 0.5% | 0.20 | 0.14 | 0.32 | 0.24 | 0.44 | 0.30 | 0.55* | 0.17* |
| | 1.0% | 0.20 | 0.16 | 0.37 | 0.37 | 0.47 | 0.39 | 0.51 | 0.37 |

TABLE 4

| Vickers hardness after enamel decalcification | | | | | | |
|---|---|---|---|---|---|---|
| Pentasodium phytate (%) | | | 0 | | 1.0 | |
| Stannous pyrophosphate (%) | | | 0 | 1.0 | 0 | 1.0 | 2.0 |
| Solution pH | 4.0 | Initial | 123 | 108 | 208 | 230 | 218 |
| | | 7 days | 93 | 84 | 153 | 178 | 172 |
| | 5.0 | Initial | 108 | 98 | 209 | 228 | 209 |
| | | 7 days | 63 | 70 | 139 | 162 | 170 |
| | 6.0 | Initial | 83 | 92 | 108* | 147 | 143 |
| | | 7 days | 80 | 82 | 78* | 122 | 126 |

*Tin is completely dissolved in a solution and hence, no precipitate is present. (Tables 2-6)

EXAMPLE 3

The following toothpastes were prepared by mixing the ingredients with water.

| | |
|---|---|
| Carboxymethyl cellulose | 1.3% |
| Ethyl parahydroxybenzoate | 0.006% |
| Stannous fluoride | 0.4% |
| Pentasodium phytate | as shown in Tables 5 & 6 |
| Sodium saccharin | 0.2% |
| Flavor | 1.0% |
| Aluminosilicate | 25.0% |
| Stannous pyrophosphate | 1.0% |
| Sodium lauryl sulfate | 2.0% |
| Glycerin | 25.0% |
| Water | Balance |
| | 100.0% |

Hydrochloric acid was used for pH adjustment.

For each toothpaste, the quantity of dissolved stannous ions and the degree of improvement of enamel acid resistance were measured both immediately after preparation and also after the solution had been stored for 30 days at 20° C. in an oxygen desiccator at 1 atmospheric pressure. The degree of improvement of enamel acid resistance was evaluated by thoroughly mixing equal weights of a toothpaste and water. A block of bovine enamel was immersed in the resulting slurry at 30° C. for 3 minutes. Following the procedure described in Example 1, the Vickers hardness of the enamel block at the surface was measured after decalcification.

The quantity of dissolved stannous ions was measured by adding two parts by weight of water to one part of a toothpaste and stirring the mixture for 2 hours. The quantity of stannous ions dissolved as a result of this 2 hour stirring was measured by the iodometric titration as described in Example 1. The measured value was converted into the corresponding solubility in the original toothpaste. It should be noted that the total quantity of stannous ions is calculated to be 0.87% provided that all stannous fluoride and stannous pyrophosphate are entirely solubilized in the toothpaste.

The results are shown in Tables 5 and 6.

TABLE 5

| Vickers hardness after enamel decalcification | | | | | | |
|---|---|---|---|---|---|---|
| Toothpaste | | Pentasodium phytate | | | | |
| pH | | 0% | 0.5% | 1.0% | 2.0% | 2.5% |
| 4.0 | Fresh paste | 112 | 133 | 164 | 180 | 189 |
| | After 30 days aging | 84 | 116 | 133 | 162 | 158 |
| 5.0 | Fresh paste | 96 | 139 | 148 | 214 | 177* |
| | After 30 days aging | 80 | 119 | 121 | 169 | 159* |

TABLE 6

| Quantity of dissolved $Sn^{2+}$ (%) | | | | | | |
|---|---|---|---|---|---|---|
| Toothpaste | | Pentasodium phytate | | | | |
| pH | | 0% | 0.5% | 1.0% | 2.0% | 2.5% |
| 4.0 | Fresh paste | 0.38 | 0.43 | 0.46 | 0.52 | 0.60 |
| | After 30 days aging | 0.36 | 0.43 | 0.47 | 0.53 | 0.58 |
| 5.0 | Fresh paste | 0.53 | 0.53 | 0.59 | 0.76 | 0.82* |
| | After 30 days aging | 0.48 | 0.53 | 0.60 | 0.75 | 0.81* |

Note:
Only the toothpaste containing 0% pentasodium phytate was aged for 10 days in an oxygen desiccator.

As seen from the results in Tables 2-6, by adding a phytate to a stannous system containing highly soluble stannous fluoride and difficultly soluble stannous pyrophosphate, the quantity of dissolved stannous ions is increased in the initial solution and maintained after aging in an oxidizing atmosphere, allowing stannous ion to fully exert its effect. The addition of the phytate can also enhance the acid resistance of tooth enamel. The effect produced by the addition of the phytate was also observed in toothpastes at relatively high pH levels.

EXAMPLES 4-6

Dentifrices

| | Example 4 | Example 5 | Example 6 |
|---|---|---|---|
| Stannous fluoride | 0.4% | 0.4% | 0.4% |
| Stannous oxalate | — | 1.0 | 1.0 |
| Stannous pyrophosphate | 1.0 | — | — |
| Pentasodium phytate | 2.5 | 2.0 | 1.0 |
| Insoluble sodium metaphosphate | 40.0 | — | 40.0 |
| Aluminosilicate | — | 25.0 | — |
| Hydroxyethylcellulose | 1.5 | — | 1.0 |
| Sodium carboxymethyl cellulose | — | 1.3 | 0.5 |
| Glycerin | 25.0 | 15.0 | 15.0 |
| Sodium lauryl sulfate | 2.0 | 2.0 | 2.0 |
| Sodium saccharin | 0.2 | 0.2 | 0.2 |
| Flavor | 1.0 | 1.0 | 1.0 |
| Ethyl parahydroxybenzoate | 0.006 | 0.006 | 0.006 |
| Water | balance | balance | balance |
| | 100.0% | 100.0% | 100.0% |

EXAMPLES 7-14

Mouthwashes (liquid)

| | Example 7 | Example 8 | Example 9 | Example 10 | Example 11 | Example 12 | Example 13 | Example 14 |
|---|---|---|---|---|---|---|---|---|
| Stannous fluoride | 0.4% | 0.4% | 0.2% | 0.2% | 0.1% | 0.1% | — | — |
| Stannous chloride dihydrate | — | — | — | — | — | — | 0.5% | 0.5% |
| Stannous pyrophosphate | 1.0 | 1.0 | 0.5 | 0.5 | 0.2 | 0.2 | 1.0 | 1.0 |
| Sodium fluoride | — | — | — | — | — | — | 0.22 | — |
| Sodium monofluorophosphate | — | — | — | — | — | — | — | 0.76 |
| Pentasodium phytate | 2.0 | 2.0 | 1.0 | 1.0 | 0.5 | 0.2 | 2.0 | 1.0 |

-continued

|  | Example 7 | Example 8 | Example 9 | Example 10 | Example 11 | Example 12 | Example 13 | Example 14 |
|---|---|---|---|---|---|---|---|---|
| Tartaric acid | 0.5 | — | — | — | — | — | — | — |
| L-ascorbic acid | — | 0.5 | — | — | 0.2 | — | 0.5 | 0.5 |
| Lactic acid | — | — | 0.5 | — | — | — | — | — |
| Malonic acid | — | — | — | 0.5 | — | — | — | — |
| Flavor | 0.5 | 0.5 | 0.5 | 0.5 | 0.25 | 0.25 | 0.5 | 0.5 |
| Sodium saccharin | 0.15 | 0.1 | 0.1 | 0.1 | 0.05 | 0.05 | 0.15 | 0.15 |
| Ethanol | 10.0 | 10.0 | 10.0 | 10.0 | 10.0 | 10.0 | 10.0 | 10.0 |
| Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| pH | 5.0 | 5.0 | 5.0 | 5.0 | 5.0 | 5.0 | 5.0 | 5.0 |

Mouthwashes were prepared by blending the ingredients with water.

EXAMPLE 15

Mouthwash (liquid)

| Stannous fluoride | 0.1% |
|---|---|
| Stannous pyrophosphate | 0.2% |
| Monocalcium phytate | 0.3% |
| L-ascorbic acid | 0.2% |
| Flavor | 0.5% |
| Sodium saccharin | 0.15% |
| Ethanol | 10.0% |
| Water | Balance |
|  | 100.0% |
| pH | 5.0 |

EXAMPLE 16

Mouthwash (liquid)

| Stannous fluoride | 0.1% |
|---|---|
| Stannous pyrophosphate | 0.2% |
| Phytic acid | 0.2% |
| Trisodium citrate dihydrate | 0.2% |
| Flavor | 0.5% |
| Sodium saccharin | 0.15% |
| Ethanol | 10.0% |
| Water | Balance |
|  | 100.0% |
| pH | 5.0 |

The mouthwashes of Examples 15 and 16 were prepared as in Example 7.

EXAMPLE 17

Mouthwash (tablet)

| Stannous fluoride | 0.2g |
|---|---|
| Stannous pyrophosphate | 0.5g |
| Pentasodium phytate | 0.5g |
| Flavor | 0.2g |
| Sodium saccharin | 0.05g |
| Mannitol | 2.0g |
| Sodium carboxymethyl cellulose | 0.05g |
| Water | some |
| pH | 5.0 |

The above ingredients were mixed and pressed into a tablet by a usual method. On use, the tablet is dissolved in 100 ml of water and the mouth is washed therewith for 30–60 seconds.

EXAMPLE 18

Mouthwash (tablet)

| Stannous fluoride | 0.1g |
|---|---|
| Stannous pyrophosphate | 0.2g |
| Phytic acid | 0.5g |
| Flavor | 0.2g |
| Sodium saccharin | 0.05g |
| Gum arabic | 2.0g |
| Corn starch | 0.5g |
| Water | some |
| pH | 5.0 |

The above ingredients were mixed and pressed into a tablet by a usual method. On use, the tablet is dissolved in 100 ml of water and the mouth is washed therewith for 30–60 seconds.

EXAMPLE 19

Disintegratable tablet

| Stannous fluoride | 4.0mg |
|---|---|
| Stannous pyrophosphate | 10mg |
| Phytic acid | 20mg |
| Flavor | 10mg |
| Sodium saccharin | 1mg |
| Corn starch | 1g |

The above ingredients were mixed and pressed into a tablet by a usual method.

EXAMPLES 20–22

Oral bands

|  | Example 20 | Example 21 | Example 22 |
|---|---|---|---|
| Stannous fluoride | 100mg | — | — |
| Stannous chloride dihydrate | — | 125mg | 125mg |
| Stannous pyrophosphate | 250mg | 250mg | 250mg |
| Pentasodium phytate | 0.5g | 0.5g | 0.3g |
| Sodium fluoride | — | 55mg | — |
| Sodium monofluorophosphate | — | — | 200mg |
| Sodium carboxymethyl cellulose | 0.5g | 0.5g | 0.5g |
| Polyvinyl alcohol | 0.5g | 0.5g | 0.5g |
| Hydroxypropyl cellulose | 9.0g | 9.0g | 9.0g |
| Polyethylene glycol 4000 | 1.0g | 1.0g | 1.0g |
| Flavor | 0.05g | 0.05g | 0.05g |

The above ingredients were dissolved in water to obtain a solution weighing 100 g. The solution was freeze dried to remove the water and formed into a film which is ready for use as an oral band. When applied to teeth, the band becomes tacky due to absorption of water in saliva and firmly adheres to the tooth surface.

EXAMPLES 23-27

Topical solutions

|  | Example 23 | Example 24 | Example 25 | Example 26 | Example 27 |
|---|---|---|---|---|---|
| Stannous fluoride | 1.2% | 1.2% | — | — | 0.6% |
| Stannous chloride dihydrate | — | — | 1.5% | 1.5% | — |
| Stannous pyrophosphate | 2.0 | 2.0 | 2.0 | 2.0 | 2.0 |
| Pentasodium phytate | 6.3 | 4.5 | 6.0 | 6.0 | 6.0 |
| Sodium fluoride | — | — | 0.66 | — | — |
| Sodium monofluorophosphate | — | — | — | 2.28 | 1.14 |
| Trisodium citrate dihydrate | — | 0.5 | — | — | — |
| Flavor | 0.5 | 0.5 | 0.5 | 0.5 | 0.5 |
| Sodium saccharin | 0.2 | 0.2 | 0.2 | 0.2 | 0.2 |
| Ethanol | 10.0 | 10.0 | 10.0 | 10.0 | 10.0 |
| Water | Balance | Balance | Balance | Balance | Balance |
| Total | 100.0 | 100.0 | 100.0 | 100.0 | 100.0 |
| pH | 3.0 | 3.0 | 3.0 | 3.0 | 3.0 |

Topical solutions were prepared by adding the ingredients to water.

EXAMPLE 28

Topical solution

| Stannous fluoride | 1.2% |
|---|---|
| Stannous pyrophosphate | 1.0% |
| Dicalcium phytate | 7.0% |
| Sodium L-ascorbate | 0.5% |
| Flavor | 0.5% |
| Sodium saccharin | 0.2% |
| Ethanol | 10.0% |
| Water | Balance |
|  | 100.0% |
| pH | 3.0 |

EXAMPLE 29

Topical solution

| Stannous fluoride | 1.2% |
|---|---|
| Stannous pyrophosphate | 1.0% |
| Phytic acid | 5.0% |
| Trisodium citrate dihydrate | 0.5% |
| Flavor | 0.5% |
| Sodium saccharin | 0.2% |
| Ethanol | 10.0% |
| Water | Balance |
|  | 100.0% |
| pH | 3.0 |

The topical solutions of Examples 28 and 29 were prepared as in Example 23.

EXAMPLES 30-36

Topical pastes

|  | Example 30 | Example 31 | Example 32 | Example 33 | Example 34 | Example 35 | Example 36 |
|---|---|---|---|---|---|---|---|
| Stannous fluoride | 1.2% | 0.4% | 1.2% | 0.4% | — | — | 0.6% |
| Stannous chloride dihydrate | — | — | — | — | 1.5% | 1.5% | — |
| Stannous pyrophosphate | 2.0 | 1.0 | 2.0 | 1.0 | 2.0 | 2.0 | 2.0 |
| Pentasodium phytate | 6.0 | 2.0 | 6.3 | 1.0 | 6.0 | 6.0 | 4.0 |
| Sodium fluoride | — | — | — | — | 0.66 | — | — |
| Sodium monofluorophosphate | — | — | — | — | — | 2.28 | 1.44 |
| Propylene glycol | 5.0 | 4.0 | 3.0 | 4.0 | 5.0 | 4.0 | 5.0 |
| Glycerin | 10.0 | 5.0 | 10.0 | 8.0 | 10.0 | 5.0 | 10.0 |
| Sorbitol | — | — | 5.0 | 5.0 | — | 5.0 | — |
| Hydroxyethyl cellulose | 3.0 | 2.0 | 2.0 | 2.0 | 3.0 | 2.0 | 3.0 |
| Xanthan gum | — | 1.0 | 1.0 | 1.0 | — | — | — |
| Flavor | 0.5 | 0.5 | 0.5 | 0.5 | 0.5 | 0.5 | 0.5 |
| Sodium saccharin | 0.2 | 0.2 | 0.2 | 0.2 | 0.2 | 0.2 | 0.2 |
| Butyl parahydroxybenzoate | 0.01 | 0.01 | 0.01 | 0.01 | 0.01 | 0.01 | 0.01 |
| Polyoxyethylene sorbitan monolaurate | 0.5 | 0.5 | 0.5 | 0.5 | 0.5 | 0.5 | 0.5 |
| Water | Balance | Balance | Balance | Balance | Balance | Balance | Balance |
| Total | 100.0% | 100.0% | 100.0% | 100.0% | 100.0% | 100.0% | 100.0% |
| pH | 3.0 | 4.0 | 3.0 | 4.0 | 3.0 | 3.0 | 3.0 |

Topical pastes were prepared by mixing 50 parts of water containing stannous compounds, sodium phytate and optionally fluorine compound with 50 parts of water containing the remaining ingredients.

EXAMPLE 37

Topical paste

| Stannous fluoride | 1.2% |
|---|---|
| Stannous pyrophosphate | 1.0% |
| Monocalcium phytate | 7.0% |
| Sodium malonate | 1.0% |
| Propylene glycol | 5.0% |
| Glycerin | 10.0% |
| Hydroxyethyl cellulose | 3.0% |
| Flavor | 0.5% |
| Sodium saccharin | 0.2% |
| Butyl parahydroxybenzoate | 0.01% |
| Polyoxyethylene sorbitan monolaurate | 0.5% |
| Water | Balance |
|  | 100.0% |
| pH | 4.0 |

EXAMPLE 38

Topical paste

| | |
|---|---|
| Stannous fluoride | 1.2% |
| Stannous pyrophosphate | 0.5% |
| Monomagnesium phytate | 7.0% |
| Trisodium citrate dihydrate | 0.5% |
| Propylene glycol | 5.0% |
| Glycerin | 10.0% |
| Hydroxyethyl cellulose | 3.0% |
| Flavor | 0.5% |
| Sodium saccharin | 0.2% |
| Butyl parahydroxybenzoate | 0.01% |
| Polyoxyethylene sorbitan monolaurate | 0.5% |
| Water | Balance |
| | 100.0% |
| pH | 3.0 |

The topical pastes of Examples 37 and 38 were prepared as in Example 30.

What is claimed is:

1. An oral composition for caries prophylaxis, comprising: a highly soluble stannous compound selected from the group consisting of stannous fluoride, stannous chloride, stannous chloride fluoride, sodium stannous fluoride, potassium stannous fluoride, stannous acetate, stannous hexafluorozirconate, stannous sulfate, stannous tartrate, stannous gluconate and mixtures thereof, said highly soluble stannous compound being present in the range of 0.03% to 5% by weight of the composition as stannous tin; a difficulty soluble stannous compound selected from the group consisting of stannous pyrophosphate, stannous metaphosphate, stannous oxide, stannous oxalate, stannous phosphate and mixtures thereof, said difficulty soluble stannous compound being present in the range of 0.05% to 10% by weight of the composition as stannous tin; and 0.1% to 20% by weight of the composition of a phytic acid compound selected from the group consisting of phytic acid, sodium phytate, potassium phytate, lithium phytate, ammonium phytate, magnesium phytate, zinc phytate, calcium phytate, aluminum phytate, phytin, double salts thereof and mixtures thereof, said composition being acidic.

2. The oral composition according to claim 1, wherein a portion of the difficulty soluble stannous compound is in a precipitate form.

3. The oral composition according to claim 1, wherein the highly soluble stannous compound is stannous fluoride in an amount of 0.08 to 3% by weight of the composition, and the difficultly soluble stannous compound is stannous pyrophosphate in an amount of 0.1 to 3% by weight of the composition.

4. The oral composition according to claim 1, wherein the phytic acid compound is present in an amount of 0.5 to 5% by weight of the composition.

5. The oral composition according to claim 1, wherein said phytic acid compound is selected from the group consisting of phytic acid, sodium phytate, potassium phytate, lithium phytate, ammonium phytate, magnesium phytate, calcium phytate, double salts thereof and mixtures thereof.

6. The oral composition according to claim 1 or 2 in the form of a toothpaste.

7. The oral composition according to claim 1 or 2, in the form of a liquid mouthwash.

8. The oral composition according to claim 1 or 2, in the form of a mouthwash tablet.

9. The oral composition according to claim 1 or 2, in the form of a disintegratable tablet.

10. The oral composition according to claim 1 or 2, in the form of oral bands.

11. The oral composition according to claim 1 or 2, in the form of topical solutions.

12. The oral composition according to claim 1 or 2, in the form of a topical paste.

13. The oral composition according to claim 1 or 2, wherein a fluorine compound selected from the group consisting of sodium fluoride, potassium fluoride, lithium fluoride, ammonium fluoride, sodium monofluorophosphate, sodium hydrogen monofluorophosphate, potassium monofluorophosphate, ammonium monofluorophosphate, potassium hexafluorotitanate, potassium hexafluorozirconate and mixtures thereof is present in the composition in an amount capable of supplying 50 to 10,000 parts per million of fluorine ions.

14. The oral composition according to claim 13, wherein said fluorine compound is present in the composition in an amount capable of supplying 20–10,000 parts per million of fluorine ion.

15. The oral composition according to claim 1 or 2, wherein the composition has a pH of 2 to 7.

16. The oral composition according to claim 15, wherein the pH is 3 to 6.

* * * * *